United States Patent [19]
Ward et al.

[11] Patent Number: 4,999,284
[45] Date of Patent: Mar. 12, 1991

[54] ENZYMATICALLY AMPLIFIED PIEZOELECTRIC SPECIFIC BINDING ASSAY

[75] Inventors: Michael D. Ward, Newark; Richard C. Ebersole, Wilmington, both of Del.

[73] Assignee: E. I. Du Pont de Nemours and Company, Wilmington, Del.

[21] Appl. No.: 178,366

[22] Filed: Apr. 6, 1988

[51] Int. Cl.[5] ............ C12Q 1/00; G01N 33/53; C12N 13/00
[52] U.S. Cl. .......................... 435/4; 435/6; 435/7.8; 435/21; 435/28; 435/173; 435/817; 435/7.92; 435/7.94; 436/501; 436/531; 436/532; 436/537; 436/544; 436/547; 436/806; 204/403
[58] Field of Search ............ 435/4, 7, 6, 21, 28, 435/173, 817; 436/501, 531, 532, 537, 544, 547, 806; 204/1 T, 403

[56] References Cited

U.S. PATENT DOCUMENTS

| | | | |
|---|---|---|---|
| 4,030,995 | 6/1977 | Starkweather | 435/21 |
| 4,236,983 | 12/1980 | Rice | 23/230 |
| 4,444,892 | 4/1984 | Malmros | 436/806 |
| 4,830,959 | 5/1989 | McNeil et al. | 435/7 |

FOREIGN PATENT DOCUMENTS 0215669  3/1987  European Pat. Off. .......... 41/8

OTHER PUBLICATIONS

Oellerich, "Enzyme-Immunoassay", Journal of Clinical Chemistry and Clinical Biochemistry, vol. 22, 1984, 895–904.
Schmid, Dialog Abstract (1988), DBA Accession #88-06816.
R. D. Schmid, Trends in Biosensors, 1988, *Biofutur*, pp. 37–41.
Ebersole et al., J. Am. Chem. Soc., vol. 110, No. 26, pp. 8623–8628, (1988).
Shons et al., J. Biomed. Mater. Res., vol. 6, pp. 565–570 (1972).
Roederer et al., Analytical Chemistry, vol. 55, (1983).
Ngeh-Ngwainbi et al., J. Mat. Chem. Soc., vol. 108, pp. 5444–5447, (1986).
Grabbe et al., G. Electroanal. Chem., vol. 223, pp. 67–78, (1978).

*Primary Examiner*—Robert A. Wax
*Assistant Examiner*—William H. Beisner

[57] ABSTRACT

A quartz crystal microbalance assay in which the binding of analyte to a surface on or near a quartz crystal microbalance (QCM) is detected by a conjugate which comprises an enzyme capable of catalyzing the conversion of a substrate to a product capable of accummulating on or reacting with a surface of the QCM leading to a mass change and, hence, a change in resonant frequency.

28 Claims, 8 Drawing Sheets

ENZYMATICALLY AMPLIFIED PIEZOELECTRIC SPECIFIC BINDING ASSAY

FIELD OF THE INVENTION

The present invention relates to an enzymatically amplified piezoelectric specific binding assay in which analyte suspected of being present in a liquid sample is bound either on or in the proximity of a quartz crystal microbalance by means of a capture reagent, and the bound analyte is reacted with an anti-analyte reagent-/enzyme conjugate. The conjugate is reacted with a substrate specific for the enzyme to form a product that is capable of either reacting with and/or accumulating on the surface of the quartz crystal microbalance. The mass change on the surface of the quartz crystal microbalance resulting from these reactions results in a change in the resonant frequency of the quartz crystal microbalance, which can be used to determine the analyte concentration in the sample.

BACKGROUND OF THE INVENTION

The use of quartz crystal microbalances (also known as piezoelectric oscillators) in immunoassays has been described previously. These devices consist of single crystal wafers sandwiched between two electrodes. The electrodes are provided with means for connecting these devices to an external oscillator circuit that drives the quartz crystal at its resonant frequency. This frequency is dependent on the mass of the crystal, as well as the mass of any layers confined to the electrode areas of the crystal. Thus, the frequency is altered by changes in mass on the surface of the electrodes or in any layers on those electrodes. In general, the change in resonant frequency of these devices can be correlated to the amount of mass change; if the quartz crystal microbalance and any attached layers obey rigid-layer behavior, the mass change can be determined from the frequency change by the Sauerbrey relationship $$\Delta f = - \frac{2 f_0^2 \Delta m}{A \sqrt{p_q \mu_q}}$$

where $\Delta f$ is the measured frequency shift $f_0$ the parent frequency of the quartz crystal, $\Delta m$ the mass change, $A$ the piezoelectrically active area, $p_q$ the density of quartz (2.648 g cm$^{-3}$) and $u_q$ the shear modulus (2.947×10$^{11}$ dynes cm$^{-2}$ for AT-cut quartz).

Shons et al. describe a piezoelectric quartz crystal microbalance which has been modified for the determination of antibody activity in solution. A quartz crystal, precoated with antigen, is exposed to antisera of varying concentration and specificity. Antisera specific for the antigen coating will form an additional protein layer on the crystal. The thickness of the antibody layer, measured by the frequency shift of the dry crystal, is proportional to the concentration of specific antibody in solution. [J. Biomed. Mater. Res., Vol 6, pp. 565–570 (1972)].

U.S. Pat. No. 4,235,983, issued to Rice on Dec. 2, 1980, discloses a method for the determination of a particular subclass of antibody. The method utilizes a piezoelectric oscillator having bound to its surface an antigen specific for the antibody to be determined. The antigen-coated oscillator is exposed to a solution containing an unknown amount of the antibody. After the antibody in the solution is attached to the antigen on the oscillator, the oscillator is exposed to a so-called sandwiching substance which selectively binds to a specific subclass of the antibody being determined. The frequency of the oscillator is measured in the dry state before and after exposure to the sandwiching substance. The change in frequency is related to the amount of the subclass of antibody bound to the oscillator, and the amount of the subclass of antibody in the solution can be determined by reference to a standard curve.

Roederer et al. disclose an in-situ immunoassay using piezoelectric quartz crystals, specifically, surface acoustic wave devices. Goat anti-human IgG was immobilized on the quartz crystal surface with a coupling agent. The piezoelectric crystals were then placed in an electric oscillator circuit and tested for detection of the antigen human IgG. Detection was based upon the fact that surface mass changes by adsorption are reflected as shifts in the resonant frequencies of the crystals The authors concluded that the method suffers from both poor sensitivity and poor detection limits. The authors also concluded that the antigen to be detected must be of high molecular weight; low molecular weight analytes cannot be directly detected by this methodology. [Analytical Chemistry, Vol. 55, (1983)].

Ngeh-Ngwainbi et al. describe the use of piezoelectric quartz crystals coated with antibodies against parathion which are used for the assay of parathion in the gas phase. When the coated antibody binds with parathion by a direct reaction in the gas phase, the resulting mass change on the crystal generates a frequency shift proportional to the concentration of the pesticide. [J. Mat. Chem. Soc., Vol. 108, pp. 5444–5447 (1986)].

European patent application 0 215 669, published Mar. 25, 1987, discloses an analytical device and method for the in-situ analysis of biochemicals, microbes and cells. Again, the method is predicated on a resonant frequency change caused by a weight change on the surface of a piezoelectric crystal on which are immobilized receptor materials specific for the analyte to be detected.

Grabbe et al. describe a quartz crystal resonator, used in conjunction with cyclic voltammetry, to study the binding of human IgG and anti-IgG at a silver electrode. [G. Electroanal. Chem Vol 223, pp. 67–78 (1987)].

As discussed by Roederer et al., piezoelectric crystal-based immunoassays in which mass change is attributable only to the immunological reaction between an antigen and an antibody can, under certain circumstances, suffer from poor sensitivity and poor detection limit. Consequently there is a need in the art for a piezoelectric crystal-based specific binding assay in which the reaction between a binding agent and its ligand can be amplified to provide a more sensitive and reliable assay.

SUMMARY OF THE INVENTION

This need is met by the present invention which, in one aspect, is a process for measuring an analyte utilizing a conjugate comprising an enzyme and either an anti-analyte reagent or the analyte. The conjugate is capable of reacting with (or competing with) an analyte indirectly bound to a quartz crystal microbalance by a capture reagent that is directly bound to a surface of the quartz crystal microbalance. The quartz crystal microbalance may have at least one of its surfaces modified by any combination of chemically reactive, priming, coating or anti-analyte layers prior to exposure to the analyte. Such a modified quartz crystal microbalance is referred to herein as a biologically modified quartz crystal microbalance, or BMQCM. Once the conjugate is bound to the BMQCM-bound analyte, a substrate specific for the enzyme is added to the system. The enzyme catalyzes a reaction in which the substrate is converted to a product which either (1) accumulates on the surface of the BMQCM; (2) reacts with and is subsequently incorporated into the BMQCM, either electrostatically, covalently or by simple adsorption; or (3) reacts with the BMQCM, but results in incorporation of a species other than the enzymatic reaction product. The resulting mass changes produce corresponding changes in the resonant frequency of the quartz crystal, as measured by an external oscillator circuit and frequency meter In another aspect, the present invention is a process for measuring an analyte utilizing a reaction chamber in which a quartz crystal microbalance is placed opposite and in close proximity to a surface having capture reagent adsorbed thereon. Upon exposure to the sample, analyte is bound by the capture reagent. The resulting bound complex is then reacted with a conjugate comprising an enzyme and either an anti-analyte reagent or the analyte. A substrate is then introduced. The enzyme catalyzes a reaction in which the substrate is convered into a product which accumulates on the surface of the quartz crystal microbalance, thereby changing its mass and resonant frequency. The accumulation of product on the microbalance can be mediated by a reactive layer on the microbalance. The reactive layer can be chosen to mediate mass accumulation by, for example, physical adsorption, ion complexation or covalent attachment of the catalysis product. Alternatively, the reactive layer can be chosen so that the catalysis product causes a change in the reactive layer that results in simple adsorption, ion exchange or covalent attachment of another reagent in the reaction medium.

BRIEF DESCRIPTION OF THE DRAWING

The drawing consists of eight figures.

DETAILED DESCRIPTION OF THE INVENTION

The invention may be understood by reference to the Drawing wherein like reference numerals are used to indicate like elements.

Figure 1:
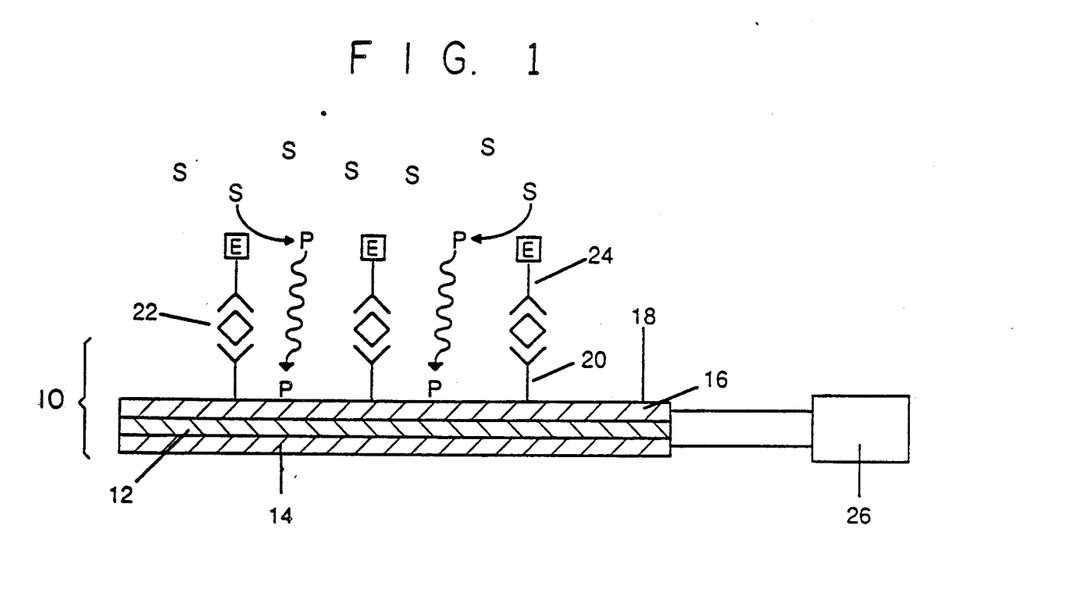
FIGS. 1 through 7 depict various modes of carrying out the present invention.

Referring now to FIG. 1, there is seen a biologically modified quartz crystal microbalance (BMQCM) indicated generally by the reference numeral 10. The BMQCM comprises a quartz crystal wafer 12 sandwiched between two electrodes 14, 16. Adsorbed to one surface 18 of the electrode 16 is capture reagent 20.

Upon exposure of the BMQCM having capture reagent bound thereto to a solution (not shown) containing analyte 22, the analyte 22 will be bound by the adsorbed capture reagent 20, thus forming a bound complex. After a suitable incubation period, unbound analyte is washed away.

The QCM is then contacted with a conjugate 24 comprising anti-analyte reagent and an enzyme, designated generally by E. After a suitable incubation period, unbound conjugate is washed away.

The QCM, having the conjugate bound thereto, is then contacted with a solution containing a substrate, designated generally by S, which is specific for the enzyme E. The enzyme will then catalyze a reaction in which the substrate is converted to a product P. The enzyme and substrate system is chosen such that the product P is insoluble and precipitable on the BMQCM surface. The product P will accumulate on the surface 18, thereby leading to a change in mass and hence a change in resonant frequency, as measured by an external circuit 26.

Suitable anti-analyte reagents and capture reagents include those reagents which are capable of participating in complexation reaction with the analyte. Preferred reagents include antibodies, lectins, chelating agents, binding proteins, DNA and RNA polynucleic acid probes, and cell receptors. The choice of reagent will depend on the analyte to be measured. The anti-analyte reagent and capture reagent may be the same or different chemically.

Suitable analytes include proteins, hormones, enzymes, antibodies, drugs, carbohydrates, nucleic acids, etc.

Examples of enzyme/substrate systems which are capable of producing an insoluble product which is capable of accumulating on the surface of the BMQCM include alkaline phosphatase and 5-bromo-4-chloro-3-indolylphosphate (BCIP). The enzymatically catalyzed hydrolysis of BCIP produces an insoluble dimer which precipitates on the surface of the BMQCM. Other analogous substrates having the phosphate moiety replaced with such hydrolytically cleavable functionalities as galactose, glucose, fatty acids, fatty acid esters and amino acids can be used with their complementary enzymes.

Other enzyme/substrate systems include peroxidase enzymes, for example horseradish peroxidase (HRP) or myeloperoxidase, and one of the following: benzidene, benzidene dihydrochloride, diaminobenzidene, o-tolidene, o-dianisidine and tetramethylbenzidene, carbazoles, particularly 3-amino-9-ethylcarbazole, all of which have been reported to form precipitates upon reaction with peroxidases. Also, oxidases such as alphahydroxy acid oxidase, aldehyde oxidase, glucose oxidase, L-amino acid oxidase and xanthine oxidase can be used with oxidizable substrate systems such as a phenazine methosulfate-nitriblue tetrazolium mixture.

Figure 2:
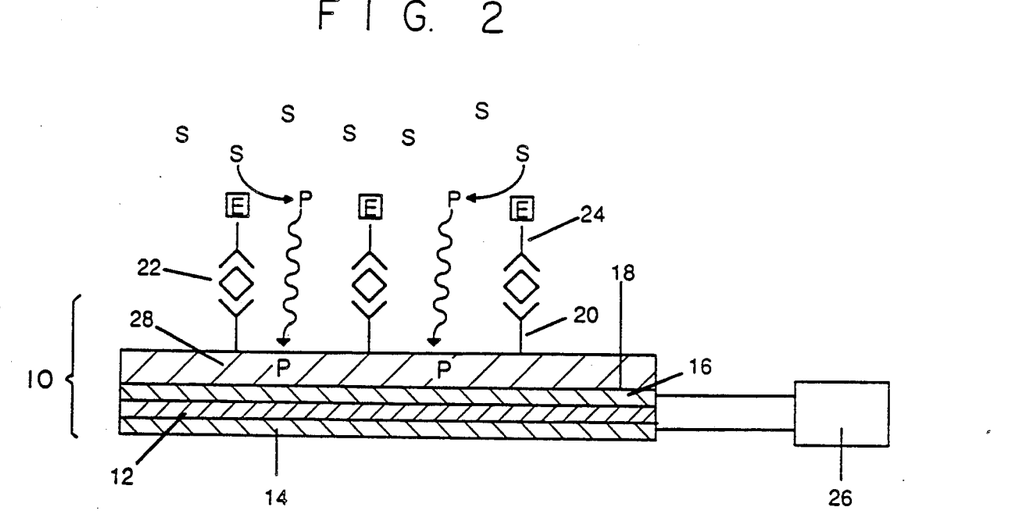

Referring now to FIG. 2, there is seen an alternative embodiment of the BMQCM shown in FIG. 1. Specifically, the surface 18 has been modified by coating it with a layer 28. The layer 28 can serve as a "priming" layer, which enhances attachment of the capture reagent 20. The layer 28 can also serve to enhance mass accumulation on the BMQCM by (1) specific reaction between product P and the layer 28, (2) ion exchange between P and the layer 28 or (3) simple absorption of P into the layer 28.

Illustrative surfaces 28 are polymer films and silane reagents that serve to enhance the binding of the capture reagent during equilibration by either hydrophobic interactions or covalent interactions. An example of a polymer film is polystyrene, which, itself, can be applied by conventional methods, such as spin coating. Higher surface area coatings for greater capture reagent coverages can be achieved by fabrication of irregular and three dimensionally shaped surfaces, such as by aerosol application which deposits minute droplets of polymer. Suitable silanes include the general class of alkyl trichlorosilanes, which covalently bind to the metal and glass surfaces of the quartz crystal microbalance by M-O-Si and Si-O-Si linkages, respectively. The general class of aminosilanes, when attached to the QCM surface via M-O-Si or Si-O-Si linkages, can be used to bind the capture reagent by covalent linkages between the nitrogen atom of the aminosilane and an appropriate functional group on the capture reagent. Surfaces can also be treated with reactive films, for example, redox polymer films such as polyvinylferrocene, PV-Fc, which serve as hydrophobic layers to enhance binding of the capture reagent, as well as reactive layers that react with the enzymatic reaction product, P, leading to an increased mass and changed resonant frequency.

Examples of enzyme/substrate systems which result in the production of a product for which the BMQCM surface can have a specific affinity include horseradish peroxidase and hydrogen peroxide/iodide mixtures. In this system, the substrate is catalytically converted by the enzyme to $I_2/I_3^-$ which oxidizes a PV-Fc film on the surface of the BMQCM. After oxidation, $I_3^-$ is specifically bound by the PV-Fc$^+$ sites in the film.

Figure 3:
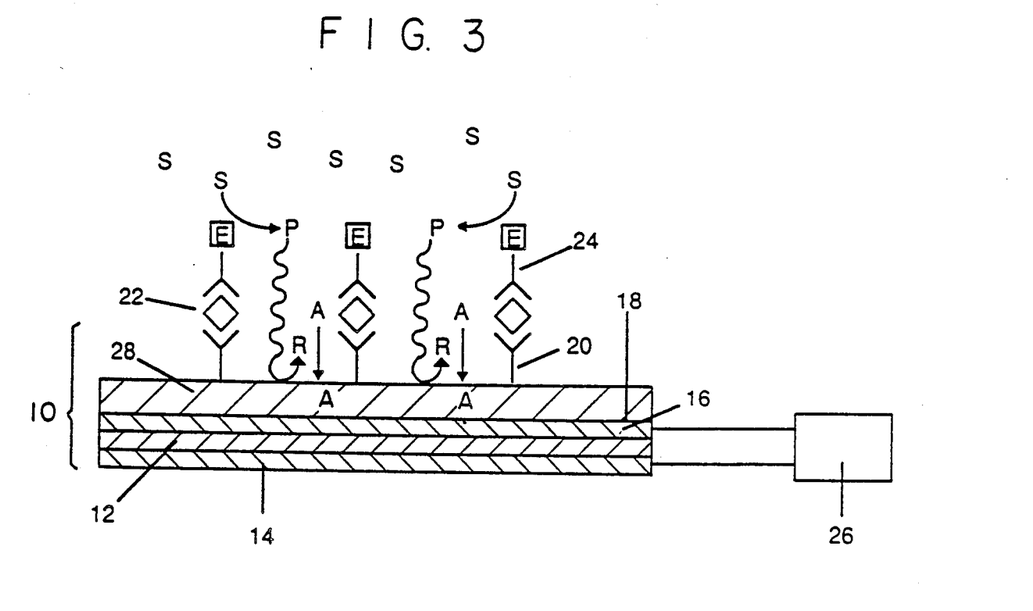

Referring now to FIG. 3, there is seen yet another embodiment of the BMQCM. Specifically, a layer 28 is chosen to react with the product P to induce a chemical change in the layer 28 making it specifically reactive with a chemical species, designated generally by A, which is different from P and is present in the reaction system.

Suitable layers 28 for the embodiments shown in FIGS. 2 and 3 could comprise organic thin films, redox polymers and conducting polymers which are capable of incorporating anions upon oxidation. Illustrative organic redox polymers and thin films are polyvinylferrocene, polypyrrole, polythiophene, polyacetylene and phthalocyanines. Suitable anions for the embodiment shown in FIG. 3 include halides, polyhalides, ferro/ferricyanide and nitrate. Illustrative enzyme/substrate systems are peroxidase/$H_2O_2$/$I^-$ and peroxidase/ferrocyanide.

Figure 4:
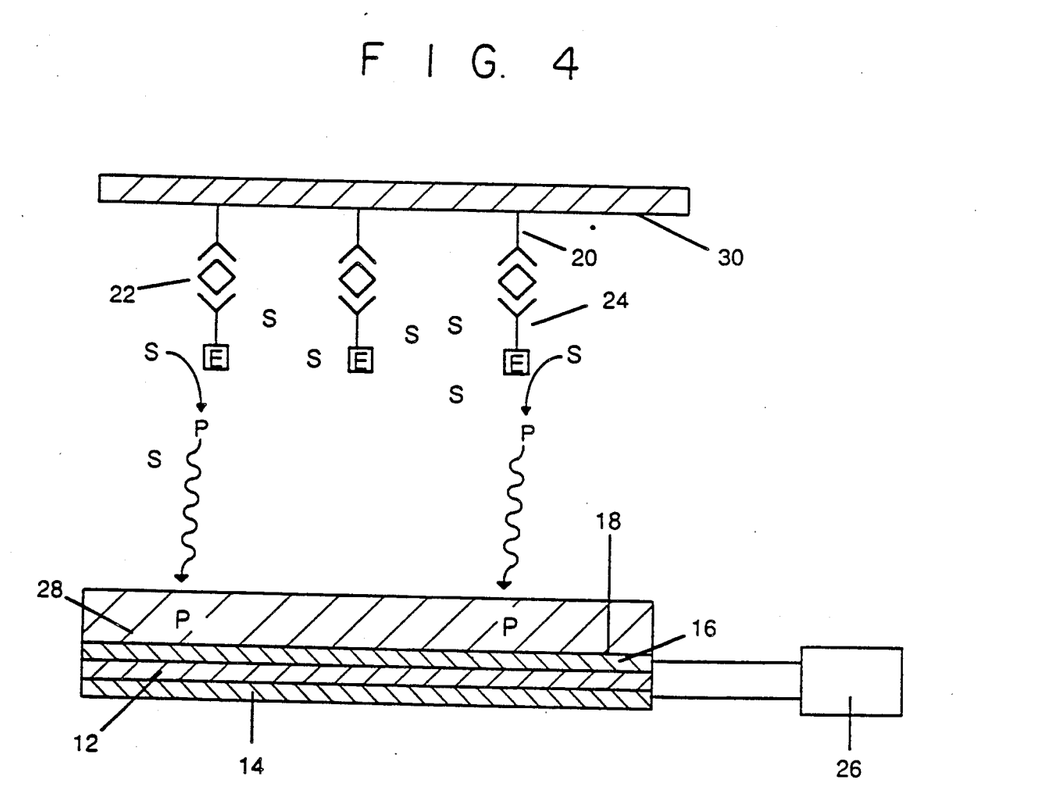

Referring now to FIG. 4, there is seen an alternative embodiment of the method according to the present invention. In this embodiment, the capture reagent 20 is attached to a support surface 30 which is different from the QCM surface 18 or layer 28. However, the support surface 30 must be in close proximity to the layer 28. In this embodiment, analyte 22 is bound by capture reagent 20 The bound analyte is then reacted with conjugate 24. The conjugate 24 is then reacted with substrate S to produce product P which diffuses to layer 28 where it accumulates to produce a mass change and, hence, a resonant frequency change.

Figure 5:
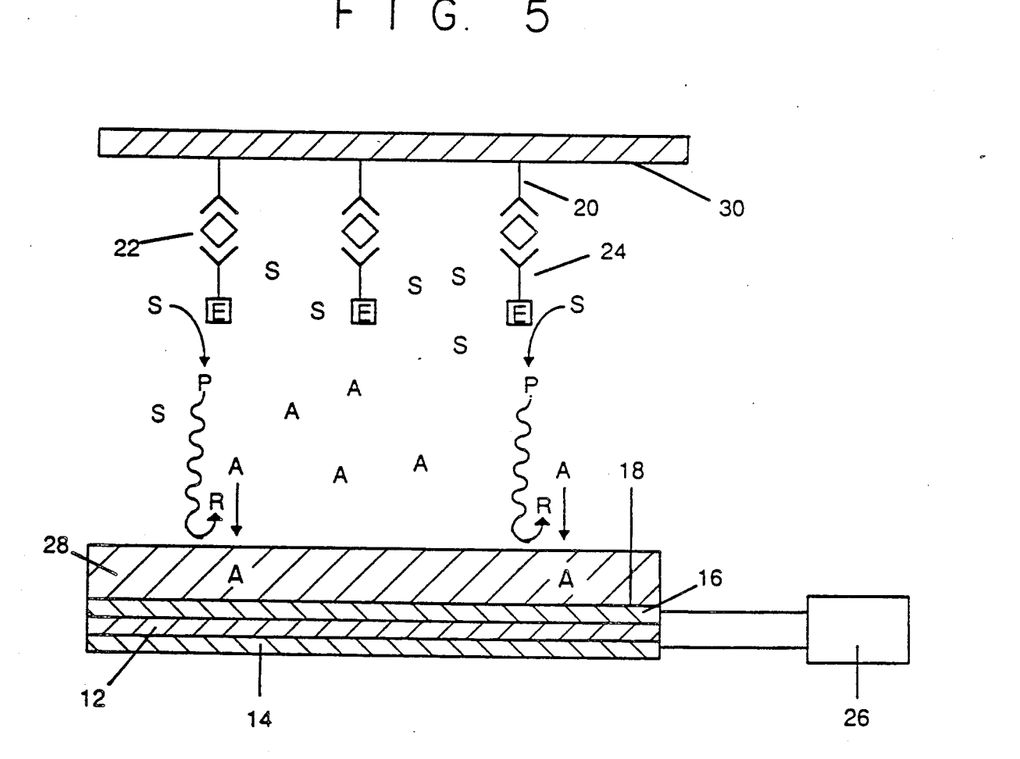

FIG. 5 depicts substantially the same embodiment, except that the interaction of the product P with the layer 28 induces a chemical change in the layer 28, making it reactive with a species A present in the reaction system. Suitable layers 28, enzyme/substrate systems and species A have been discussed above in connection with FIG. 3.

Figure 6:
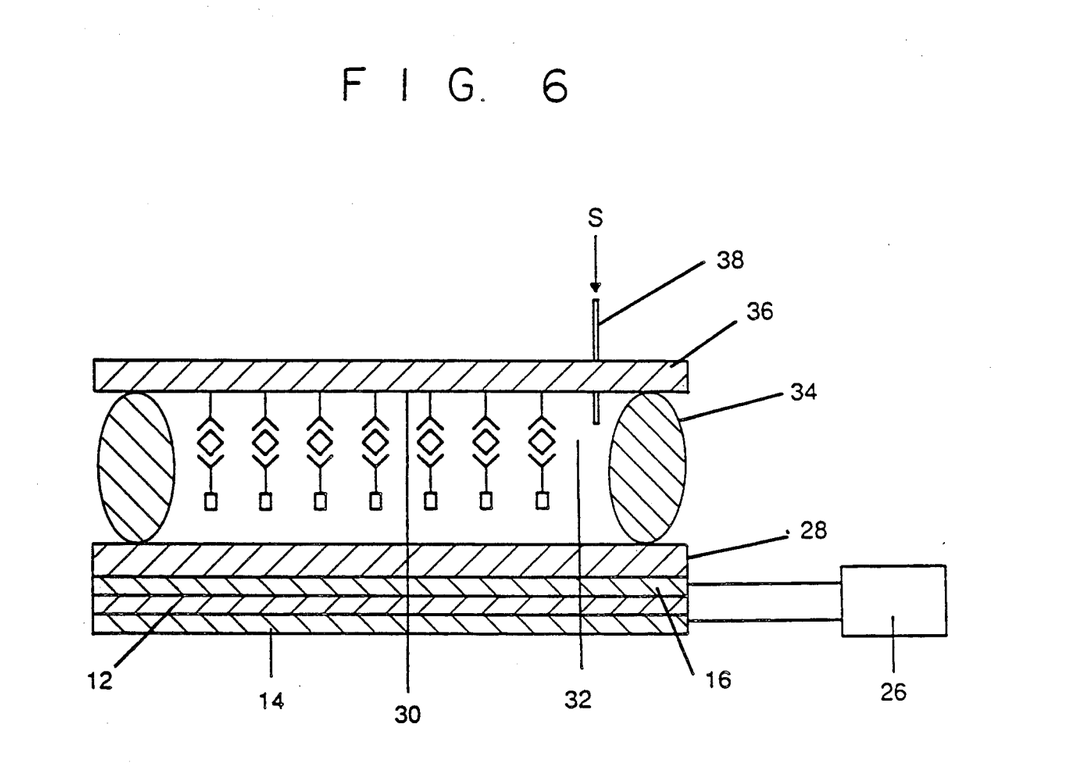

FIG. 6 depicts a simple device for carrying out the assays described in FIGS. 4 and 5. The QCM is mounted at the bottom of a chamber 32 so that its reactive layer 28 is exposed to the interior of the chamber The side walls of the chamber are formed by an o-ring 34. At the top of the chamber is a nylon support mesh 36 which provides support surface 30. Adsorbed on surface 30 is capture reagent 20. In use, the nylon mesh 36 is incubated in any convenient vessel (not shown) with the sample solution. After a suitable incubation, the mesh 36 is washed and reacted with conjugate 24. After a suitable incubation, the mesh 36 is washed and placed on the top of chamber 32. The substrate S can then be introduced into the chamber 32 by a suitable inlet tube 38.

For the embodiments described in FIGS. 4 5 and 6, suitable support surfaces include porous and nonporous polymeric thin films, cellulosic membranes and nitrocellulose membranes. The reactive films 28 may include organic thin films, polymers, redox polymers and conducting polymers which are capable of adsorbing the product P or reacting with P, followed by incorporation of P or a different species A. The polymers or organic thin films may include polyvinylferrocene, polypyrrole, polythiophene, polyacetylene and phthalocyanines. Illustrative anions are halides, polyhalides, ferro/ferricyanide and nitrate. An illustrative enzyme/substrate system is peroxidase/$H_2O_2$/$I^-$. In this enzyme/substrate system, peroxidase catalyzes the conversion of $I^-$ to $I_2/I_3^-$, which, in turn, oxidizes a polyvinylferrocene film. Subsequent incorporation of $I_3^-$ in the film to maintain charge balance results in a mass increase and a measurable change in frequency of the QCM.

In the description relating to FIGS. 1 through 5, above, the sample and reagents are described as being added sequentially. It should be understood, however, that the reagents may be added simultaneously.

Figure 7:
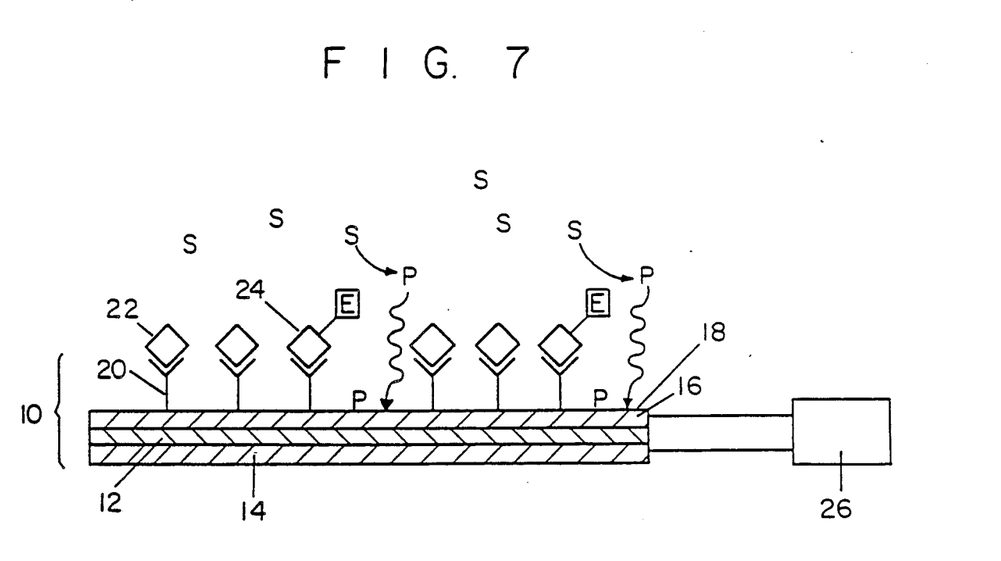

FIG. 7 depicts another embodiment of the invention in which the analyte 22 and a conjugate of analyte and enzyme 24 compete for a limited number of capture reagent 20 sites on the surface of the QCM. The sample can be added before the conjugate 24 or together with the conjugate 24. After a suitable incubation period, the unbound conjugate 24 is washed away, and substrate added. The remainder of the assay is performed as described above. In this case, the response due to accumulation of mass on the BMQCM is inversely proportioned to the analyte concentration. It should be understood that this embodiment may also be performed using a capture reagent surface which is in proximity to the surface of the QCM, analogous to the embodiments shown in FIGS. 4 and 5.

Figure 8:
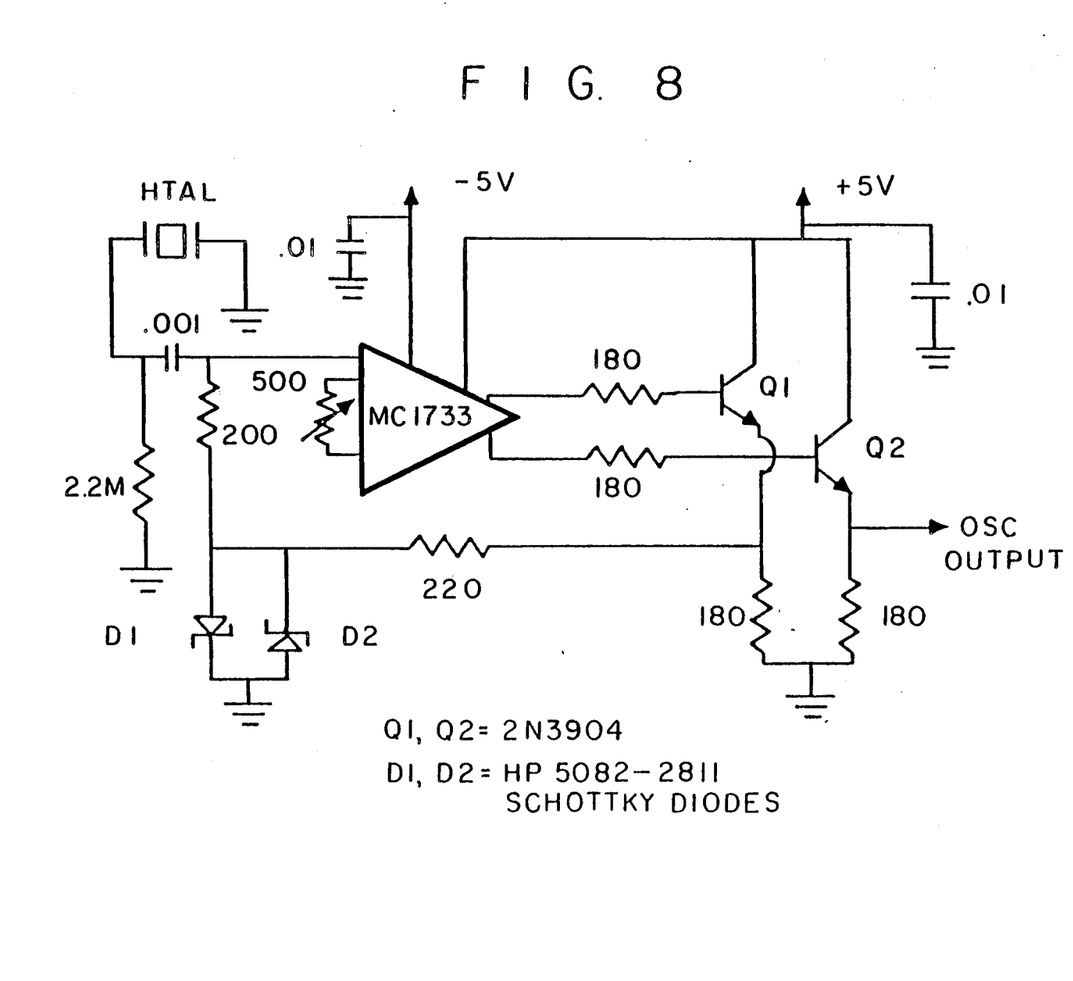
FIG. 8 depicts suitable circuitry for measuring the resonant frequency of the BMQCM.

FIG. 8 depicts circuitry which may be used to measure the resonant frequency of the BMQCM. Such circuitry is conventional and well-known in the art.

In general, attachment of the capture reagent 20 is accomplished by incubation of the QCM in a phosphate buffered saline (PBS) buffer solution of the capture reagent, in concentrations ranging from 50 to 100 ug/ml, depending on the capture reagent and the type of surface on the quartz crystal microbalance. Another suitable method involves immobilization of the capture reagent by chemical crosslinking, for example with glutaraldehyde. After equilibration, the BMQCM is washed with PBS buffer solution to remove any excess capture reagent that is not strongly attached to the desired surface.

After formation of the BMQCM assembly, the BMQCM is exposed to solutions of the analyte 22 at room temperature for a period of time predetermined to be optimal for the capture reagent/analyte system under study. After this exposure, the surface is washed with TRIS test buffer to remove non-specifically adsorbed material. The conjugate 24 is then added in concentrations ranging from 0.05 to 20 ug/mL in TRIS test buffer to the BMQCM/analyte assembly at room temperature. Conjugate can be prepared, for example, according to the method of Imagawa [J. Biochem., 92, 1413 (1982)] or Avrameas et al. [Scand. J. Immunol., Vol. 8, Suppl. 7, 7-23 (1978)] and maintained at 4° C. as a stock solution. Conjugates of enzymes and synthetic polynucleic acids can be prepared according to the method of Ruth et al. [DNA, 4, 93 (1985)]. This is then followed by washing with TRIS test buffer solution to remove nonspecifically adsorbed conjugate 24. The total amount of conjugate 24 should be added at a concentration to exceed the amount of specifically adsorbed analyte 22. Alternatively, the analyte and conjugate may be added simultaneously.

In a so-called competitive mode, the analyte and an analyte/enzyme conjugate may be reacted with the BMQCM The analyte and conjugate may be added sequentially or simultaneously.

The frequency of the quartz crystal microbalance is measured in 50 MM TRIS wash buffer solution, and then a standard solution of the substrate is directly added. The rate of frequency change, as well as the total frequency change after a time considered to be the optimum measurement interval, are measured in solution and, since conjugate is present only when analyte is bound to the surface, are indicative of the amount of analyte exposed to the BMQCM. The signal measured is amplified by the large turnover numbers of the enzymatic reaction, which produces concentrations of product far exceeding that of the analyte.

The present invention can be embodied in diagnostic kits comprising crystals treated with the desired capture reagent and any modifying layers 28, and an oscillator circuit with direct readout of the resonant frequency of the quartz crystal microbalance. In typical use, the analyte solution, for example patient serum, would be added to a compartment containing the BMQCM, followed by a wash with buffer solution, followed by addition of the appropriate enzyme/anti-analyte reagent conjugate, followed by a wash. The substrate would then be added and the frequency change directly measured. The preferred mode of operation would include the use of a reference crystal which is exposed to the identical solutions, but which has not been modified so as to have capture reagent on or in proximity to its surface. In this manner, the difference in frequency between the sample and reference crystals can be measured and errors due to changes in viscosity, temperature and non-specific binding minimized. Operation with only the sample crystal, however, is also feasible, because (1) the viscosity and temperature changes during addition of the substrate and during measurement are not large, (2) interference from nonspecific adsorption is minimized by the washing step, and (3) the measurement step poses no risk of mass changes from processes other than those induced by P.

The invention is further illustrated by the following nonlimiting examples.

EXAMPLE 1

Assay of adenosine-5'-phosphosulfate (APS) reductase using alkaline phosphatase/5-bromo-4-chloro-3-indolylphophate (BCIP) on unmodified quartz crystals The procedure was performed according to the mode illustrated in FIG. 1, with anti-APS reductase antibody as the capture reagent 20, APS reductase as the analyte 22, anti-APS reductase antibody with alkaline phosphatase enzyme as the conjugate 24, and 5-bromo-4-chloro-3-indolylphophate (BCIP) as the substrate, S. The first step was adsorption of the anti-APS antibody on the gold/quartz surfaces of a quartz crystal. This was performed by equilibration of the gold/quartz crystal with 2 mL of 100 ug/mL anti-APS reductase antibody in PBS buffer solution for 2 hours. The crystal was then washed once with PBS buffer containing 0.1% bovine serum albumin (BSA) and then 3 times with PBS buffer to remove excess anti-APS reductase antibody and block any nonspecific binding sites. The crystal was then exposed to varied concentrations of APS reductase ranging from 0 to 400 ng in 1.5 mL of TRIS test buffer solution for 20 minutes; the dosage concentrations were varied to determine the response characteristics of the device. After being washed with TRIS test buffer to remove nonspecifically adsorbed APS reductase, the crystal was exposed for twenty minutes to 1.5 mL TRIS test buffer solution containing 30 mL conjugate comprised of anti-APS reductase antibody and alkaline phosphatase enzyme. The crystal was then washed again 2 times with test buffer and once with 50 MM TRIS wash solution.

The detection step was performed by immersing the crystal in 0.5 mL of TRIS wash buffer in a cell holder, followed by addition of 0.5 mL of a standard solution of BCIP reagent solution (SIGMA). A positive response for antigen was measured by a decrease in frequency, corresponding to the precipitation of the oxidized dimer of BCIP, an indigo dye analog. Precipitation results from the enzymatically catalyzed hydrolysis of the phosphate functionality of BCIP, which, in turn, only occurs if the alkaline phosphatase conjugate is present, which, in turn, is only possible when the APS reductase is present. Table 1 indicates the frequency response of the BMQCM to different dosage levels of APS reductase. It is clear that the frequency change and the rate of change increase with larger dosage rates, as expected. The relative responses agreed with those determined by the spectroscopically measured optical density of the blue BCIP indigo dimer deposited on the surface 18 of the quartz crystal microbalance. Notably, these responses were observed for APS reductase levels in which the direct binding of APS reductase could not be observed. That is, the frequency change resulting from addition of APS reductase to the BMQCM was not detectable.

TABLE 1

| APS reductase concentration (ng/mL) | Δ frequency/sec (Hz/sec) | Δ frequency in 30 min. |
|---|---|---|
| 200 | 0.24 | 406 |
| 75 | 0.17 | 250 |
| 25 | 0.10 | 170 |
| 7.5 | 0.002 | 6.3 |

EXAMPLE 2

Assay of APS using alkaline phosphatase/5-bromo-4-chloro-3-indolylphophate (BCIP) on quartz crystals with polyvinylferrocene modifying layers The procedure was performed according to the mode illustrated in FIG. 2, with a polyvinylferrocene (PVFc) layer 28 on the quartz crystal, an anti-APS reductase antibody as the capture reagent 20, APS reductase as the analyte 22, anti-APS reductase antibody with alkaline phosphatase enzyme as the conjugate 24, and 5-bromo-4-chloro-3-indolylphophate (BCIP) as the substrate, S. The PV-Fc layer serves as a hydrophobic layer, enhancing adsorption of the anti-APS reductase antibody.

The first step was adsorption of the anti-APS reductase antibody onto a PV-Fc layer, applied by spin coating from a 10% o-chlorotoluene solution onto the gold-/quartz surface 18 of a quartz crystal. This was performed by equilibration of the PV-Fc modified gold-/quartz crystal with 1.5 mL of 100 ug/mL anti-APS reductase antibody in PBS buffer solution for 2 hours. The crystal was then washed 3 times with PBS buffer to remove excess anti-APS reductase antibody. The crystal was then exposed to 0 to 80 mL of APS reductase (0.5 mg/mL) in 2 mL TRIS test buffer solution for 30 minutes; the dosage rate was varied to determine the response characteristics of the device. After being washed with TRIS test buffer to remove nonspecifically adsorbed APS reductase, the crystal was exposed for thirty minutes to 1.5 mL TRIS test buffer solution containing 30 mL of conjugate comprised of anti-APS reductase antibody and alkaline phosphatase enzyme. The crystal was then washed again with TRIS test and TRIS wash buffers as described in Example 1.

The detection step was performed by immersing the crystal in 0.5 mL of TRIS buffer in a cell holder, followed by addition of 0.5 mL of a standard detection solution containing 50% dilution of BCIP substrate reagent (SIGMA) in 50 MM TRIS buffer (SIGMA). A positive response for antigen was measured by the decrease in frequency, corresponding to the precipitation of the oxidized dimer of BCIP, an indigo dye analog. Precipitation results from the enzymatically catalyzed hydrolysis of the phosphate functionality of BCIP, which, in turn, only occurs if the alkaline phosphatase conjugate is present, which, in turn, is only possible when the APS reductase is present. Table 2 indicates the frequency response of the BMQCM to different dosage levels of APS reductase. It is clear that the frequency change and the rate of change increase with larger dosage rates, as expected. The relative responses agreed with those determined by the spectroscopically measured optical density of the blue BCIP indigo dimer deposited on the surface 18 of the quartz crystal microbalance.

TABLE 2

| APS reductase concentration (ng/mL) | Δ frequency/sec (Hz/sec) | Δ frequency in 30 min. |
|---|---|---|
| 200 | 0.22 | 278 |
| 75 | 0.09 | 80 |
| 25 | 0.05 | 69 |
| 7.5 | 0.025 | 22 |

EXAMPLE 3

Assay of human chorionic gonadotropin (hCG) using horseradish peroxidase/hydrogen peroxide-iodide on nylon membranes situated opposite to a quartz crystal microbalance modified with polyvinylferrocene modifying layers The procedure was performed according to the mode illustrated in FIGS. 4 and 6, with a polyvinylferrocene (PV-Fc) layer 28 on the quartz crystal situated opposite to a nylon membrane 36 whose surface 30 was modified with capture reagent. The spacing of the compartment was approximately 1 mm. In this example, anti-hCG antibody was the capture reagent 20, hCG was the analyte 22, anti-hCG antibody with horseradish peroxidase (HRP) enzyme was the conjugate 24, and a hydrogen peroxide-iodide mixture was the substrate, S. The nylon membrane served as a hydrophobic layer that adsorbed the anti-hCG antibody, and presented the enzymatic reaction product to the PV-Fc film. The enzymatically catalyzed formation of iodine/triiodide that occured when the conjugate was present resulted in oxidation of the PV-Fc film, followed by incorporation of triiodide into the film to maintain electroneutrality. This led to an increase in mass of the PV-Fc film and accordingly a large change in the resonant frequency of the BMQCM device.

The first step was adsorption of the anti-hCG antibody to the nylon surface 30 of membrane 36. This was performed by equilibration of the nylon membrane 30 with 2 mL of 100 ug/mL anti-hCG antibody in PBS buffer solution for 2 hours. The membrane was then washed once with PBS buffer containing 0.1% BSA and then 3 times with PBS buffer to remove excess anti-hCG antibody and block any nonspecific binding sites. The membrane was then exposed for thirty minutes to different concentrations of hCG in PBS buffer containing 0.1% BSA buffer solution. After being washed with PBS buffer to remove nonspecifically adsorbed hCG antigen, the membrane was exposed for twenty minutes to 2 mL buffer solution containing 20 mL of stock conjugate comprised of anti-hCG antibody and HRP enzyme. The membrane was then washed again with PBS/0.1% BSA buffer solution.

The detection step was performed by placing the membrane opposite to the quartz crystal modified with the PV-Fc film, with a 1 mm diameter separator between the two surfaces to form a reaction compartment. The compartment was filled with a pH=5.0 citrate/phosphate/iodide detection buffer. After the frequency stabilized, 10 mL of a standard solution of 0.01% hydrogen peroxide was added. The enzymatically catalyzed reaction product iodine/triiodide, P, diffuses across the compartment to the PV-Fc film, resulting in oxidation of the PV-Fc film by one-half of an equivalent of P. This is subsequently followed by incorporation of an equivalent of triiodide into the oxidized PV-Fc film, resulting in an increase in mass of the film and a corresponding decrease in resonant frequency of the quartz crystal microbalance. Triiodide incorporation results from the enzymatically catalyzed conversion of iodide to iodine/triiodide, which, in turn, only occurs if the HRP conjugate is present, which, in turn, is possible only when the hCG antigen is present.

TABLE 3

| hCG concentration (ng/ml) | Δ frequency/sec (Hz/sec) | Δ frequency in 10 min. |
|---|---|---|
| 0 | <0.005 | <3 |
| 600 | 0.01 | 48 |

The invention is defined by the following claims, although it will be appreciated by those skilled in the art that various modifications can be made without departing from the spirit thereof.

What is claimed is:

1. In a process for detecting an analyte suspected of being present in a liquid sample, which process comprises reacting the sample with a quartz crystal microbalance (QCM) having an analyte capture reagent bound to a surface thereof thereby binding the analyte to the QCM by the analyte capture reagent, the improvement comprising reacting the bound analyte with (1) a conjugate comprising an enzyme and either an anti-analyte reagent or the analyte, and (2) a substrate which is catalyzed by the enzyme to form a product which accumulates on or reacts with the QCM surface to induce a mass change, thereby leading to a resonant frequency change of the QCM.

2. The method of claim 1 wherein the conjugate comprises an enzyme and an anti-analyte reagent.

3. The method of claim 1 wherein the analyte capture reagent is an antibody, lectin, chelating agent, binding protein, polynucleic acid probe, or cell receptor 4. The method of claim 3 wherein the analyte capture reagent is an antibody or polynucleic acid probe.

5. The method of claim 4 wherein the analyte capture reagent is an antibody.

6. The method of claim 1 wherein the anti-analyte reagent is an antibody, lectin, chelating agent, binding protein, polynucleic acid probe, or cell receptor.

7. The method of claim 3 wherein the analyte capture reagent is an antibody or polynucleic acid probe.

8. The method of claim 4 wherein the analyte capture reagent is an antibody.

9. The method of claim 1 wherein the enzyme is alkaline phosphatase and the substrate is 5-bromo-4-chloro-3-indolylphosphate.

10. The method of claim 1 wherein the enzyme is horseradish peroxidase.

11. The method of claim 1 wherein the surface is coated with a silane, polymer or organic thin film.

12. The method of claim 11 wherein the polymer is polyvinylferrocene, polypyrrole, polythiophene, polyacetylene or phthalocyanine.

13. The method of claim 12 wherein the enzyme is horseradish peroxidase and the substrate is hydrogen peroxide/iodide, urea peroxide/iodide or ferrocyanide.

14. The method of claim 13 wherein the substrate is hydrogen peroxide/iodide.

15. A method for detecting an analyte suspected of being present in a liquid sample, comprising reacting the sample with a support surface having an analyte capture reagent bound thereon, said support surface being in close proximity to the surface of a quartz crystal microbalance, and reacting the support surface with a (1) conjugate comprising an enzyme and either an anti-analyte reagent or the analyte and (2) a substrate which is catalyzed by the enzyme to form a product which accumulates on or reacts with the QCM surface to induce a mass change, thereby leading to a resonant frequency change of the QCM.

16. The method of claim 15 wherein the conjugate comprises an enzyme and an anti-analyte reagent.

17. The method of claim 15 wherein the analyte capture reagent is an antibody, lectin, chelating agent, binding protein, polynucleic acid probe, or cell receptor.

18. The method of claim 16 wherein the analyte capture reagent is an antibody or polynucleic acid probe.

19. The method of claim 17 wherein the analyte capture reagent is an antibody.

20. The method of claim 15 wherein the anti-analyte reagent is an antibody, lectin, chelating agent, binding protein, polynucleic acid probe, or cell receptor.

21. The method of claim 17 wherein the analyte capture reagent is an antibody or polynucleic acid probe.

22. The method of claim 18 wherein the analyte capture reagent is an antibody.

23. The method of claim 15 wherein the enzyme is horseradish peroxidase.

24. The method of claim 15 wherein the quartz crystal microbalance surface is coated with a silane, polymer or organic thin film.

25. The method of claim 24 wherein the polymer is polyvinylferrocene, polypyrrole, polythiophene, polyacetylene or phthalocyanine.

26. The method of claim 25 wherein the enzyme is horseradish peroxidase and the substrate is hydrogen peroxide/iodide, urea peroxide/iodide or ferrocyanide.

27. The method of claim 26 wherein the substrate is hydrogen peroxide/iodide.

28. The method of claim 15 wherein the support surface is nylon or nitrocellulose.

* * * * *